United States Patent [19]

Allen, Jr.

[11] Patent Number: 4,636,315
[45] Date of Patent: Jan. 13, 1987

[54] FLUID SEPARATOR APPARATUS AND METHOD

[75] Inventor: Crowley C. Allen, Jr., Durham, N.C.

[73] Assignee: Research Triangle Institute, Research Triangle Park, N.C.

[21] Appl. No.: 768,862

[22] Filed: Aug. 23, 1985

Related U.S. Application Data

[62] Division of Ser. No. 448,201, Dec. 9, 1982, Pat. No. 4,537,217.

[51] Int. Cl.⁴ .................. B01D 15/08; B01D 53/04; B01D 53/18
[52] U.S. Cl. .................................... 210/656; 55/67; 55/74; 55/386; 55/387; 210/660; 210/767; 210/198.2; 210/289
[58] Field of Search ............... 55/386, 1, 67, 74, 387; 210/656, 659, 767, 807, 198.2, 289, 291, 446, 456, 660, 350–352

[56] References Cited

U.S. PATENT DOCUMENTS

| | | | |
|---|---|---|---|
| 2,647,634 | 8/1953 | Barton | 210/350 |
| 3,796,657 | 3/1974 | Pretorius et al. | 210/198.2 |
| 3,814,253 | 6/1974 | Forsberg | 210/198.2 |
| 3,966,609 | 6/1976 | Godbille et al. | 210/198.2 |
| 4,077,880 | 3/1978 | Lorenz et al. | 210/807 |

Primary Examiner—Ivars Cintins
Attorney, Agent, or Firm—Bell, Seltzer, Park & Gibson

[57] ABSTRACT

A fluid distributor comprises a distributor body having a fluid port at one face and a distribution surface at the opposite face, with the distribution surface having a plurality of uniformly spaced distribution openings. Fluid passages defined by channels and bores in the distributor body provide fluid communication between the fluid port and the distribution openings such that there is substantially equal fluid flow to each distribution opening. A method of fluid distribution particularly adapted for chromatography applications is also disclosed.

7 Claims, 12 Drawing Figures

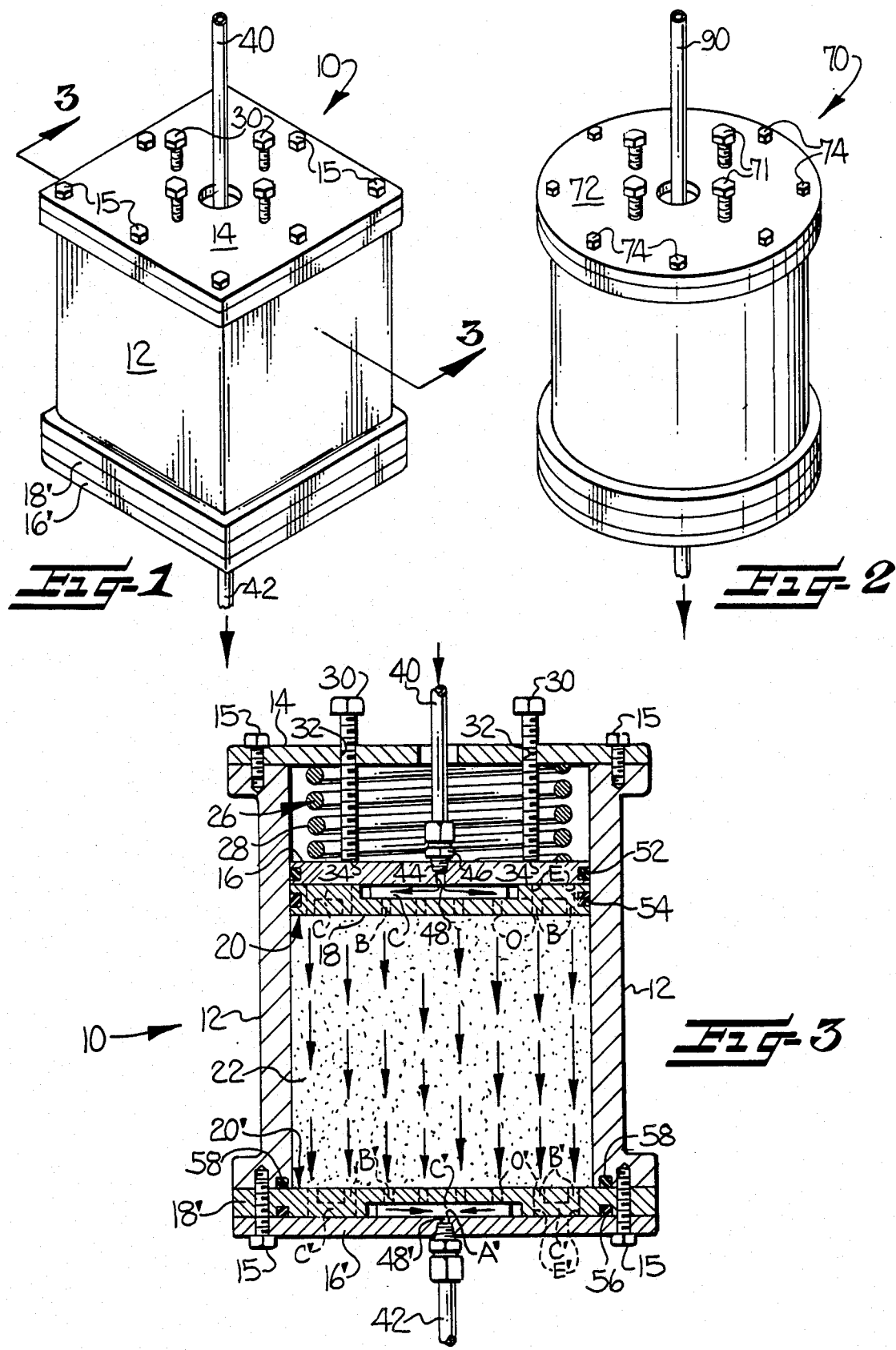

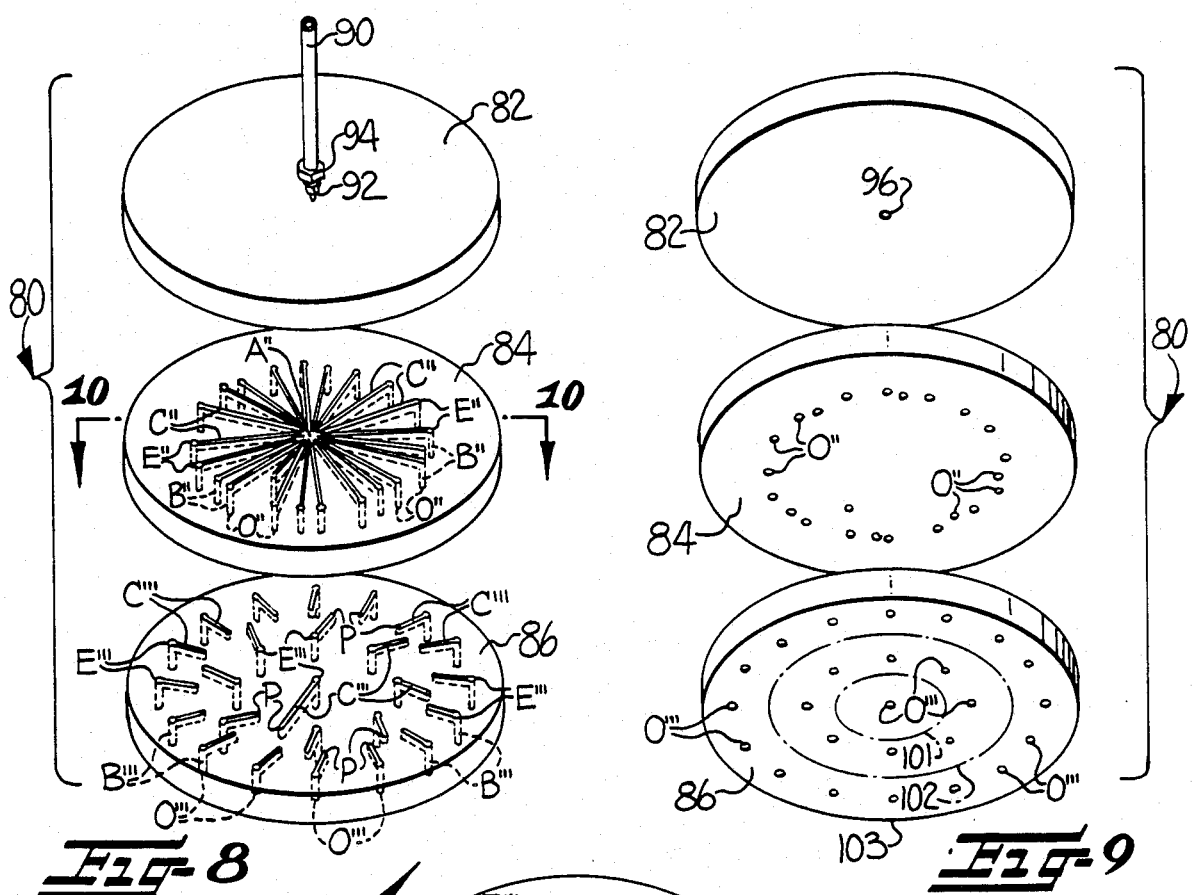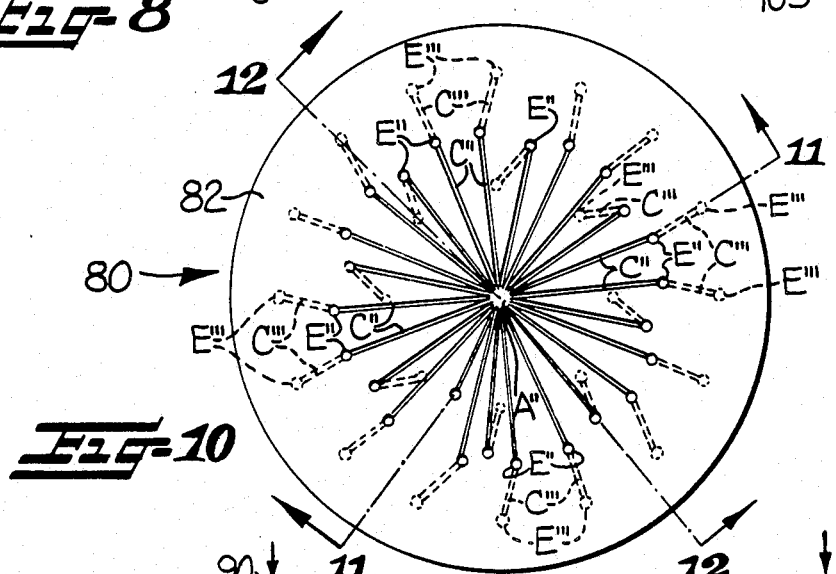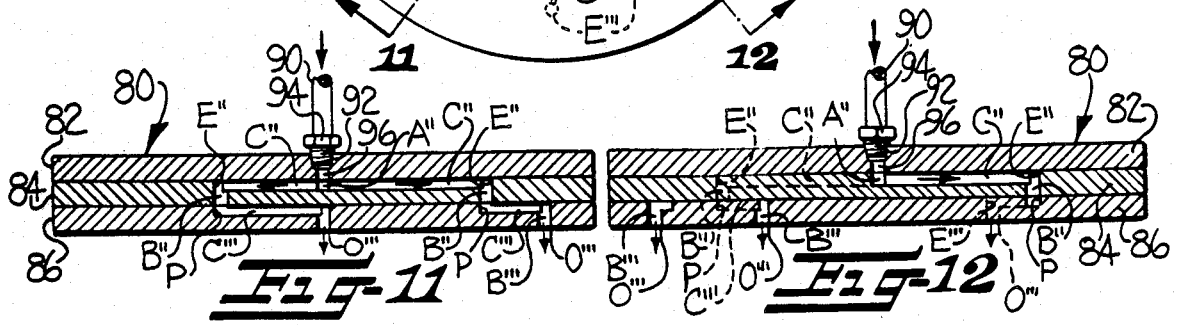

FLUID SEPARATOR APPARATUS AND METHOD

This application is a division of application Ser. No. 448,201 filed Dec. 9, 1982, now U.S. Pat. No. 4,537,217.

BACKGROUND OF THE INVENTION

1. Field of the Invention

The present invention relates to the uniform distribution of fluid at a distribution surface. In particular embodiments the invention relates to fluid distribution of the type occurring in separation procedures such as liquid chromatography, gas chromatography, ion exchange, distillation and absorption.

2. Description of the Prior Art

In separation procedures, particularly in liquid chromatography, the fluid distribution system is critical to the overall performance, and becomes more so as the cross-section of the chromatographic column increases.

Columns used in liquid chromatography typically comprise a body-forming structure enclosing a packing through which a carrier liquid flows, with separation taking place by material distribution between the carrier liquid and the packing. Ideally, the carrier liquid is uniformly introduced throughout the surface at the top of the column, flows through the packing at the same velocity throughout the packing cross section, and is uniformly removed at the plane defined by the bottom of the column.

Conventional distribution systems for use in liquid chromatography must address a number of inherent problems that have deleterious effects on the separation efficiency of the column. Among these problems are nonuniform initial fluid distribution at the top of the column, disruption of the surface of the bed and "channeling" within the bed.

With respect to the channeling problem, conventional distribution systems often rely upon the pressure drop in the distributor of a vertical chromatographic column to distribute the fluid uniformly horizontally. Whenever the pressure drop through the column is high relative to the pressure drop in the distributor, however, the fluid tends to channel in the center of the column causing excessive dispersion. This severely limits the effectiveness of chromatographic separations and is particularly acute for large diameter columns.

The problem of nonuniform initial fluid distribution refers generally to the problem of providing a uniform initial fluid flow at the top of the separation column. Without a uniform introduction of fluid in the plane defined by the top of the column, it is virtually impossible to achieve uniform flow distribution through the packing.

The problem of disruption of the surface of the bed stems in large part from systems that include a dead volume of fluid at the top of the column. It is desirable to have a system that permits adjustable positioning of the fluid distributor at the top of the column so that the location of the distributor can be changed with changes in column packing, thereby greatly reducing or eliminating the dead volume of fluid at the top of the column.

One well-known system for fluid distribution in liquid chromatography applications utilizes fritted discs as the distribution elements. Fritted discs are typically used in high pressure liquid chromatography (HPLC) applications wherein high pressures are used to achieve fluid distribution through the extremely small openings in the fritted discs. Such systems pose the problem of supporting the fritted discs under such pressure, particularly where the surface area of the fritted disc is comparatively large as in large-diameter column applications.

Another well-known technique for distribution is the plate system, typically utilizing a plate with face openings along radii on the plate to achieve the fluid distribution. A drawback of the plate system is that the spacing and size of the openings in the plate must be calculated for any particular fluid according to its viscosity and other physical characteristics (the rheology of the fluid) so that the system will work properly with that particular fluid at a particular flow rate. A drawback to the plate system, however, is that variation in the fluid being distributed or the flow rate will affect the uniformity of the distribution.

Despite the high level of activity in the field of chromatography over many years, and the many distribution systems proposed, both speculative as well as experimentally evaluated, the need still exists for an effective, relatively simple distribution system that will permit larger liquid chromatographic columns to be used. To date, no distribution system is available which meets this end.

SUMMARY OF THE INVENTION

In accordance with the present invention there is provided a fluid distributor that offers many advantages over distributors of the prior art. The distributor of the invention may utilize fluid passages of sufficient size to provide extremely low pressure drops across the distributor, while at the same time providing remarkably uniform distribution of fluid. The inherent low pressure drop achieved by distributors of the invention is particularly important in applications of the invention to chromatrographic columns with large cross-sectional areas. The scale-up of chromatrographic columns to extremely large sizes, for example greater than one foot in width or diameter, may be achieved due to the many advantageous features of the invention. Further, the distributors of the invention may be easily incorporated into mechanical systems for keeping the distributors in intimate contact with the packing so as to greatly reduce or eliminate the mentioned problem of a dead volume of fluid at the top of the column.

In accordance with one aspect of the invention there is provided a fluid distributor having a distribution body that defines first and second exterior portions. A fluid port is provided at the first exterior portion. The second exterior portion defines the distribution surface of the distributor and includes a plurality of uniformly distributed distribution openings. Interconnecting fluid passages extend through the distributor body for providing communication between the fluid port and each of the distribution openings in such a manner that the fluid flow path between the fluid port and each of the distribution openings is of substantially uniform length and has similar geometric flow resistance characteristics so as to provide substantially the same resistance to flow therealong. The fluid distributor may be used in either a first mode wherein fluid entering the fluid port is uniformly discharged by the distribution openings, or in a second mode wherein fluid is uniformly drawn into the distribution openings and conveyed to the fluid port.

In another aspect, the present invention comprises a fluid separation apparatus, for example a chormatographic column, including a column-forming body structure and a packing material therein. The separation apparatus further includes a pair of fluid distributors enclosing the packing within the body structure with each distributor having a distribution surface in intimate contact with the packing. A first fluid distributor is positioned at the input end of the separation apparatus for uniformly distributing fluid to the packing and a second distributor is positioned at the output end of the separation apparatus for receiving a uniform distribution of fluid from the packing.

In yet another aspect, the invention comprises a method of fluid separation wherein a fluid is uniformly distributed at the head of a column of packing material and uniformly withdrawn from the base of the packing material. The method utilizes fluid distributors in intimate contact with both the head and the base of the packing material. Each distributor has fluid passages that provide the fluid communication between the fluid port and distribution openings thereof.

BRIEF DESCRIPTION OF THE DRAWINGS

Some of the features of the invention having been stated, others will appear as the description proceeds when taken in connection with the accompanying drawings, in which FIG. 1 is a perspective view of a chromatographic column incorporating features of the present invention;

FIG. 2 is a perspective view of a second chromatographic column of a different configuration from the column shown in FIG. 1, and also incorporating features of the present invention;

FIG. 3 is a sectional view taken substantially along line 3—3 of FIG. 1 and showing a fluid distributor at both the inlet and outlet of the chromatographic column;

FIG. 8 is an enlarged perspective view of the three plates forming one of the fluid distributors incorporated in the chromatographic column illustrated in FIG. 2;

FIG. 9 is an enlarged perspective view of the plates illustrated in FIG. 8, showing the opposite faces of the plates;

FIG. 10 is a view taken in the direction of line 10—10 of FIG. 8;

FIG. 11 is a sectional view through the three plates shown in FIG. 8 and 9 as taken substantially along line 11—11 of FIG. 10; and FIG. 12 is a sectional view through the three plates shown in FIGS. 8 and 9 as taken substantially along line 12—12 of FIG. 10.

DETAILED DESCRIPTION

Figure 4:
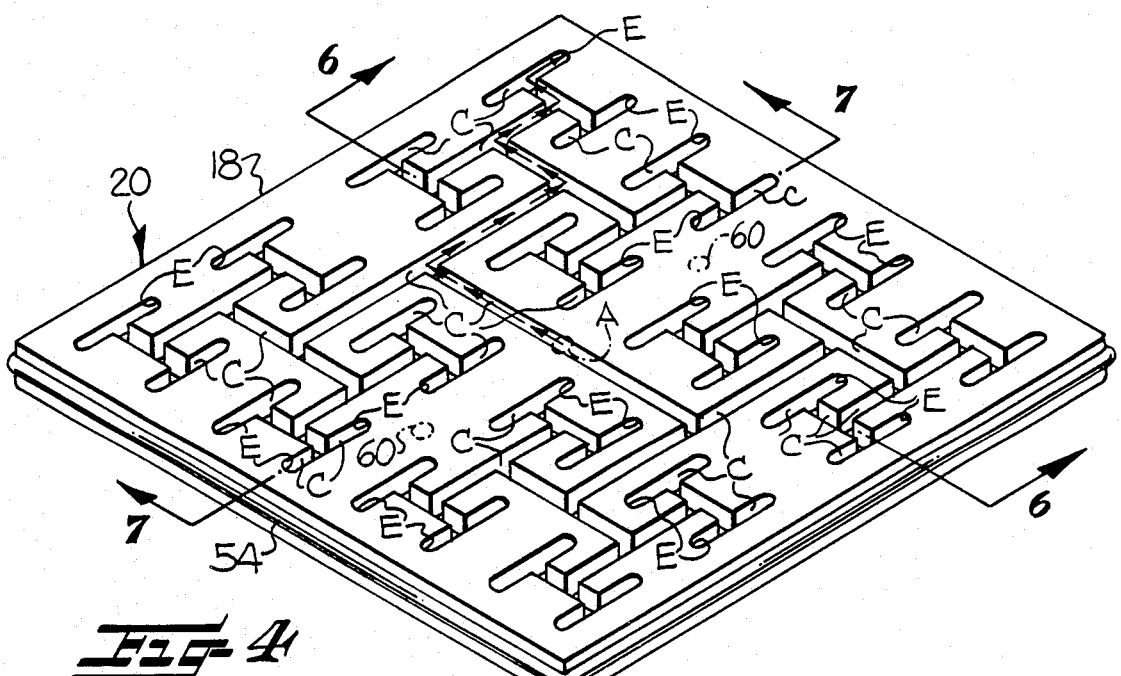
FIG. 4 is an enlarged perspective view of one of the plates of a fluid distributor incorporated into the chromatographic column of FIG. 1.
Figure 6:
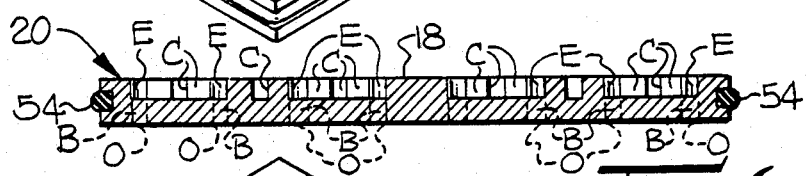
FIG. 6 is a sectional view taken substantially along line 6—6 of FIG. 4.

While the present invention will be described hereinafter with particular reference to the accompanying drawings, it is to be understood at the outset of the description which follows that it is contemplated that the present invention may be varied in specific detail while still achieving the desirable characteristics and features of the present invention. Accordingly, the description is to be understood as a broad enabling teaching directed to persons skilled in the applicable arts, and is not to be understood as restrictive.

Referring to the drawings, and particularly to FIGS. 1 and 3, there is shown a liquid chromatographic column 10 incorporating features of the present invention. Column 10 is square in cross-section and includes upper and lower fluid distributors 20 and 20', respectively.

Column 10 includes a column-forming body structure 12 enclosed at one end by an end cap 14 that is securely held in place to the body structure by means of appropriate fasteners, such as bolts 15. The opposite end of the body structure 12 is enclosed by the two plates 16', 18' of the lower fluid distributor 20'. Plates 16', 18' are secured to body structure 12 by means of bolts 15.

Column 10 has a packing 22 disposed therein. Packing 22 may be one of the many well-known packing materials used in the field of liquid chromatography. The two fluid distributors 20, 20' are held in intimate contact with the packing 22 by means of force imparted by a spring-loaded system 26. As best shown in FIG. 3, system 26 includes a coil spring 28 mounted between end plate 14 and plate 16 of upper distributor 20. System 26 may be controlled by adjustment of threaded adjustment members 30 which are threaded into threaded openings 32 in end cap 14 and have ends 34 bearing against plate 16.

Fluid is introduced into column 10 at the inlet end in the conventional manner by means of an inlet conduit 40 and exits at the outlet end through an outlet conduit 42. It will be noted that upper distributor 20 serves to distribute uniformly to the head of packing 22 the fluid entering the column, whereas the lower distributor 20' serves to receive uniformly the fluid from the base of the packing so that it may exit the column. For convenience in description, the upper distributor 20 will be described in detail with it being understood that the lower distributor 20' is substantially identical, but inverted.

Distributor 20 includes a first plate 16 having a fluid port 44 on the exterior surface thereof joined to conduit 40 by means of fitting 46. Port 44 is in fluid communication with the opposite face of plate 16 by means of an opening 48 extending through plate 16.

Plate 16 is positioned together with a second plate 18 along flat, mating planar surfaces thereof. Plates 16, 18 define the distributor body and are sealed to prevent peripheral leakage by means of seals 52, 54, respectively.

Figure 5:
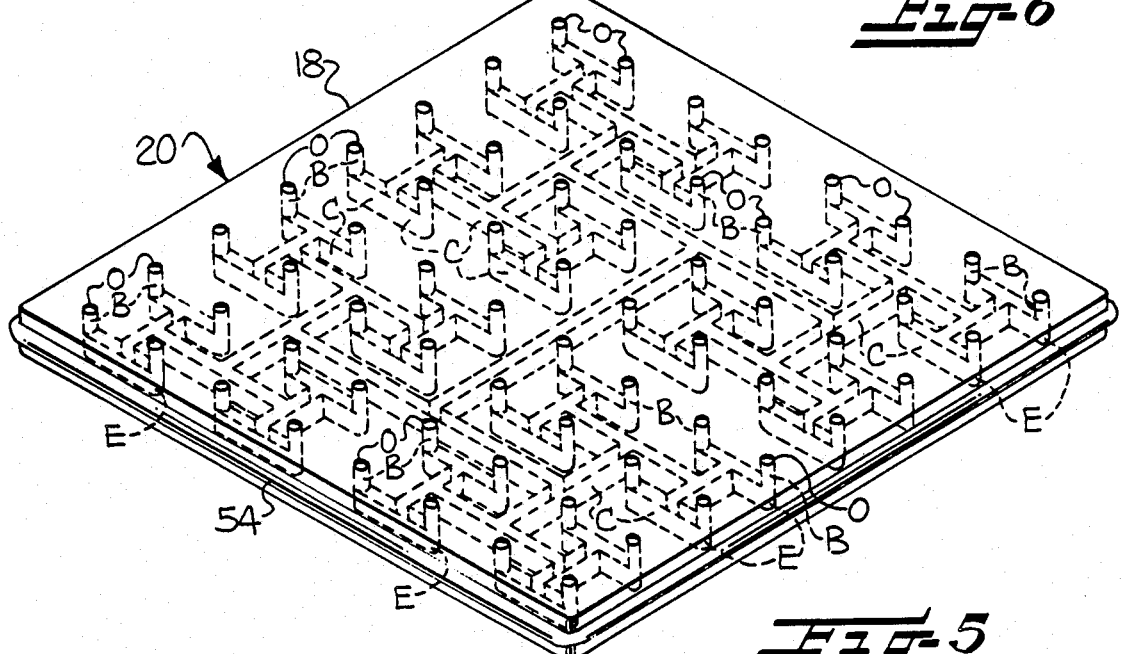
FIG. 5 is an enlarged perspective view of the opposite face of the plate shown in FIG. 4.
Figure 7:
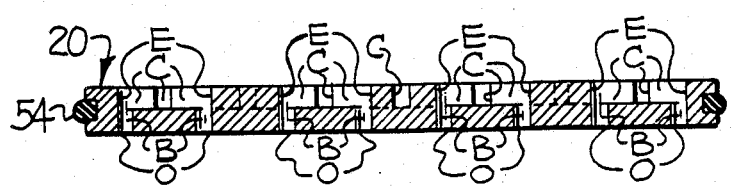
FIG. 7 is a sectional view taken substantially along line 7—7 of FIG. 4.

Referring to the top perspective view of plate 18 (FIG. 4), it can be seen that fluid passing downwardly through opening 48 in plate 16 enters a series of coplanar channels C formed in the upper surface of plate 18, with a common fluid introduction point A of the channels being substantially centrally located as shown in phantom lines in FIGS. 4 and 5. The channels formed in the face of plate 18 are enclosed by the opposed planar mating face of plate 16.

The channels C branch outwardly from the fluid introduction point A to define a selected number of unique channels paths. Each channel terminates in an end point, generally designated by the reference character E in FIGS. 4 and 5. Each end point E is an equal channel path distance from the fluid introduction point A. Due to the equal distances and similar geometric flow resistance characteristics, substantially the same resistance to fluid flow is provided along each of the paths A–E. As best shown in FIG. 5, the end points E are uniformly distributed in the plane of plate 18.

FIG. 5 shows the opposite face of plate 18 that defines a flat distribution surface and illustrates that each end point E communicates with a bore B that, in turn, communicates with a distribution opening O on the lower, exterior face of plate 18. Thus, channels C and bores B define fluid passages that extend through plate 18. Since the openings O are directly below their respective end points E on the upper face of plate 18, openings O are therefore uniformly distributed in the plane of plate 18 and serve to distribute fluid uniformly throughout such plane and into packing 22. In this context, "uniformly distributed" or "uniform distribution" is defined as the division of a surface into n sections which contain equal surface area, with each section of the surface having one opening O and with substantially equal fluid flow passing through each opening O. It will be appreciated that the quality of uniform distribution may be generally improved by increasing the number of sections n and designing the geometry of the sections so that the ratio of the perimeter to the area of each section is small. It will also be appreciated that the distribution may occur along a flat distribution surface as described above, or may occur along other distribution surface configurations such as hemispherical, parabolic, or the like.

The fluid distributed through openings O passes through packing 22 in the manner well known in the art until it reaches lower distributor 20' which serves to receive fluid from packing 20 through uniformly spaced openings O' in its respective plate 18' and pass the fluid to outlet conduit 42. Thus, in lower distributor 20' the fluid flows through the openings O', to the end points E', along channels C' to point A', and therefrom to opening 48' in plate 16' and into the outlet conduit 42.

In the particular embodiment illustrated in FIGS. 1 and 3-7, the plates are shown as being substantially square and as having flat, planar surfaces. The channels C serve to subdivide the square plate area into smaller constituent squares numbering an integral power of 4, for example, 64 as shown in the drawings, or 256, etc. such that one of the channel end points E resides approximately centrally located within each of the constituent squares. As best shwon in FIG. 4, channels C form a pattern of progressively smaller H configurations ending in the smallest H configurations, each of which defines four end points E. With embodiments employing the illustrated H configurations, the use of only one H would result in $4^1=4$ end points E; the use of two levels of H's would result in $4^2=16$ end points E; and the use of three levels of H's, as illustrated, would result in $4^3=64$ end points E.

The path from common fluid introduction point A to one of the end points E is shown by the arrows in FIG. 4. It can be seen that the fluid flow is divided by ½ at point A and then again by ½ each time a channel deadends. It will be appreciated that the flow in the channels close to point A is greater than that in the more remote channels so that the channel cross sections may be made proportional to the flow in the particular channels.

It should be pointed out that the perimeters of plates 16' and 18' of lower distributor 20' are somewhat larger than those of plates 16 and 18 of upper distributor 20 so that the peripheries of plates 16', 18' may be secured to body structure 12 by bolts 15 and thereby close the lower end of column 10. Appropriate seals 56, 58 are provided at the peripheries. Otherwise, plates 16', 18' are identical to plates 16, 18 except that they are inverted.

While the distributor body has been illustrated as comprising a pair of plates, with the channels conveniently formed at the plates' mating surfaces, it will be appreciated that the distributor body may be formed in other fashions. For example, the distributor body may be formed as a monolithic structure with the fluid passages formed therein to communicate between the fluid port and the uniformly spaced distribution openings. The fluid passages on such a monolithic structure may be formed by casting or etching techniques known in the art.

Referring to FIG. 4, an optional feature that may be incorporated into the distributor and into an associated chromatograph is the provision of openings 60 in the distributors permitting countercurrent flow of two fluids in the chromatograph. Openings 60 may be used to facilitate the countercurrent flow of a second fluid in the manner well known in the art.

Referring now to FIG. 2, there is shown a second embodiment of the present invention comprising a fluid chromatographic column 70 that is circular is cross section. Column 70 includes a spring-loaded system (not shown in the drawings), similar to that illustrated in connection with the earlier-described column 10, for holding a packing between upper and lower fluid distributors, one of which is illustrated in detail in FIGS. 8-12. The threaded adjustment members 71 for the spring-loaded system are shown in FIG. 2. Column 70 also includes an end cap 72 held in place by means of threaded fasteners 74 in a manner similar to that of the earlier described end cap of column 10.

Substantially identical distributors positioned at the top and bottom of the packing in column 70 serve to distribute fluid into the packing and thereafter receive fluid uniformly from the packing in substantially the same fashion as described in association with column 10.

The upper distributor 80 of column 70 is best illustrated in FIGS. 8 and 9 and is shown as including three stacked plates, first plate 82, second plate 84, and third plate 86. In operative position, the three plates are positioned together at their flat, planar mating surfaces to form a stack.

Fluid enters distributor 80 via an inlet conduit 90 which is joined to a fluid port 92 on the exterior surface of first plate 82 by means of a fitting 94. Port 92 communicates to the opposite face of plate 82 by means of an opening 96 that directly overlies a central, common fluid introduction point A" located on the upper surface of second plate 84.

A plurality of coplanar channels C" are formed in the upper surface of plate 84 and radiate from point A". Channels C" are enclosed by the opposed planar mating face of the plate 82 to establish substantially coplanar fluid passages for conveying fluid from point A" to the end points E" of the channels.

Each end point E" communicates through a bore B" to an underlying opening O" on the opposite face of plate 84 to extend the fluid passages.

Fluid passing from plate 84 through the openings O" flows directly into the beginning points P of a correspondingly numbered series of channels C''' formed in underlying plate 86. The channels C''' in plate 86 define substantially coplanar fluid passages, each ending in an end point E''' which communicates through a bore B''' to distribution openings O''' in the opposite face of plate 86.

The channels in plates in 84 and 86 are so formed that the fluid flow path from the port 92 in plate 82 to any one of the distribution openings on the underside of plate 86 is substantially equidistant and provides substantially the same resistance to fluid flow therealong. This condition is achieved by assuring that the sum distance of any two associated channels through which fluid flows, (one channel in plate 84 and one channel in plate 86) is substantially equal to that of any other two associated channels. This can be best seen by the top view of FIG. 10 which illustrates each of the pairs of associated channels.

In the particular embodiment shown in FIGS. 8–12, the distribution openings O''' are located within areas defined by the perimeters of three concentric circles 101, 102, 103 (FIG. 9). A single central opening O''' is located in concentric circle 101. Eight openings O''' are located in the ring lying between the perimeters of concentric circles 101 and 102. Sixteen openings O''' are located in the ring lying between the perimeters of concentric circles 102 and 103. Uniform distribution is achieved in the distribution surface because the number of openings O''' in each of the three areas is proportional to the area. For example, the ring defined by the perimeters of circles 101 and 102 has an area eight times that of the central circle 101. In a similar fashion, the area of the ring defined by the perimeters of circles 102 and 103 is sixteen times as great as that of central circle 101. Even though the openings O''' in each of the three areas are located at different radial distances from the fluid port 92, the fluid flow path to each is the same length due to the locations of the cooperating channels in plates 84 and 86.

While the present invention has been described in connection with specific embodiments thereof, it will be appreciated that numerous modifications may be made without departing from the true spirit and scope of the invention. For example, the present invention may be designed to distribute fluid in configurations other than square and circular and, thus, be adapted for use with different geometries of chromatographic column cross sections. This and other modifications are within the true spirit and scope of the invention.

What is claimed is:

1. A fluid separation apparatus comprising:
   a column-forming body structure defining an input end and an output end;
   a separation-type packing material in said body structure;
   a pair of fluid distributors enclosing said packing within said body structure and each having a distribution surface in intimate contact with the packing, said pair comprising a first fluid distributor at the input end of said apparatus for uniformly distributing fluid to the packing and a second distributor at the output end of said apparatus for receiving a uniform distribution of fluid from the packing, each said distributor comprising:
   a distributor body defining first and second opposed exterior portions;
   said first exterior portion including a fluid port;
   said second exterior portion defining a distribution surface having a plurality of distribution openings so spaced as to be uniformly distributed over the surface area thereof;
   means defined by interconnecting fluid passages in said distributor body, said means extending through said distributor body for providing communication between said fluid port and each of said distribution openings, and such that the fluid flow path between said fluid port and each of said distribution openings is of substantially uniform length and has similar geometric flow resistance characteristics so as to provide substantially the same resistance to flow therealong, said interconnecting fluid passages comprising a first set of passages that communicate directly to the fluid port and a second set of passages connecting the first set to the distribution openings;
   said distributors being so positioned that fluid entering the fluid port of the first distributor is uniformly distributed to the packing through the distribution openings of the first distributor, and fluid having passed through the packing is uniformly withdrawn through the distribution openings of the second distributor for flowing out of the apparatus via the second distributor fluid port.

2. A fluid separation apparatus as claimed in claim 1 including force imparting means for holding the first and second distributors in intimate contact with said packing.

3. A fluid separation apparatus comprising:
   a column-forming body structure defining an input end and an output end;
   a separation-type packing material in said body structure;
   a pair of fluid distributors enclosing said packing within said body structure and each having a distribution surface in intimate contact with the packing, said pair comprising a first fluid distributor at the input end of said apparatus for uniformly distributing fluid to the packing and a second distributor at the output end of said apparatus for receiving a uniform distribution of fluid from the packing, each said distributor comprising:
   a plurality of plates positioned together at similarly configured, substantially planar mating surfaces thereof to define a stack of plates, said stack including at least first and last plates that serve as the exterior plates of said stack;
   the exterior surface of the first plate of said stack having a fluid port communicating to an opening on the opposite face thereof;
   the exterior surface of the last plate defining a distribution surface of the distributor and having a plurality of distribution openings so spaced as to uniformly distributed over the surface area thereof;
   means defined by interconnecting fluid passages in said plates, said means extending through said stack of plates for providing communication between said fluid port and each of said distribution openings, and such that the fluid flow path between said fluid port and each of said distribution openings is of substantially uniform length and has similar geometric flow characteristics so as to provide substantially the same resistance to flow therealong;
   said distributors being so positioned that fluid entering the fluid port of the first distributor is uniformly distributed to the packing through the distribution openings of the first distributor, and fluid having passed through the packing is uniformly withdrawn through the distribution openings of the second distributor for flowing out of the apparatus via the second distributor fluid port.

4. A fluid separation apparatus as claimed in claim 3 including force imparting means for holding said first and second distributors in intimate contact with said packing.

5. A fluid separation apparatus comprising:
   a column-forming body structure defining an input end and an output end;
   a separation-type packing material in said body structure;
   a pair of fluid distributors enclosing said packing within said body structure and each having a flat distribution surface in intimate contact with the packing, said pair comprising a first fluid distributor at the input end of said apparatus for uniformly distributing fluid to the packing and a second distributor at the output end of said apparatus for receiving a uniform distribution of fluid from the packing, each said distributor comprising:
   first and second plates positioned together at similarly configured mating faces thereof;
   the first plate mating face including an opening extending through the first plate to a fluid port on the opposite face thereof;
   the mating face of one of said plates including a network of substantially coplanar interconnecting channels, said channels including a common fluid introduction point in fluid communication with said first plate opening;
   said channels branching outwardly from said fluid introduction point to define a selected number of unique channel paths with each path terminating in a channel end point, each end point being the same channel path distance from said fluid introduction point such that all the channel paths have substantially the same fluid flow resistance therealong; and
   a bore extending through said second plate for connecting each of said channel end points to an underlying distribution opening in the opposite face thereof, said distribution openings being uniformly distributed throughout said opposite face, with the opposite face defining the flat distribution surface of said distributor;
   said distributors being so positioned that fluid entering the fluid port of the first distributor is uniformly distributed to the packing through the distribution openings of the first distributor, and fluid having passed through the packing is uniformly withdrawn through the distribution openings of the second distributor for flowing out of the apparatus via the second distributor fluid port.

6. A fluid separation apparatus as claimed in claim 5 including force imparting means for holding said first and second distributors in intimate contact with said packing.

7. In a method of fluid separation of the type wherein a fluid is uniformly distributed at the head of a column of separation-type packing material and uniformly withdrawn from the base of the packing material, the improvement comprising:
   providing a first fluid distributor having a distribution surface with uniformly distributed distribution openings and positioning the first distributor such that the distribution surface thereof is in intimate contact with substantially the entire surface area of the head of the packing;
   introducing fluid into an inlet port of the first distributor and channeling the fluid through interconnecting fluid passages in the first distributor that provide fluid communication between the inlet port and the distribution openings such that the fluid flow path between the inlet port and each of the distribution openings is of substantially uniform length and has similar geometric flow resistance characteristics so as to provide substantially the same resistance to flow therealong;
   providing a second fluid distributor having a distribution surface with uniformly distributed distribution openings and positioning the second distributor such that the distribution surface thereof is in intimate contact with substantially the entire surface area of the base of the packing; and
   while introducing fluid into the first distributor, uniformly withdrawing fluid from the base of the packing through the distribution openings of the second distributor and conveying the withdrawn fluid to a fluid port of the second distributor by channeling the fluid through interconnecting fluid passges that provide fluid communication between the distribution openings and the fluid port such that the fluid flow path between each of the distribution openings and the fluid port is of substantially uniform length and has similar geometric flow resistance characteristics so as to provide substantially the same resistance to fluid flow therealong.

* * * * *